(12) United States Patent
Desjardin et al.

(10) Patent No.: US 12,121,261 B2
(45) Date of Patent: *Oct. 22, 2024

(54) SURGICAL ACCESS DEVICE INCLUDING ANCHOR WITH RATCHET MECHANISM

(71) Applicant: Covidien LP, Mansfield, MA (US)

(72) Inventors: Kevin Desjardin, Prospect, CT (US); Astley C. Lobo, West Haven, CT (US); Douglas M. Pattison, East Hartford, CT (US); Christopher A. Tokarz, Torrington, CT (US)

(73) Assignee: Covidien LP, Mansfield, MA (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/973,659

(22) Filed: Oct. 26, 2022

(65) Prior Publication Data

US 2023/0043500 A1 Feb. 9, 2023

Related U.S. Application Data

(63) Continuation of application No. 16/783,505, filed on Feb. 6, 2020, now Pat. No. 11,484,337.

(51) Int. Cl.
*A61B 17/34* (2006.01)
*A61B 17/00* (2006.01)

(52) U.S. Cl.
CPC ...... *A61B 17/3423* (2013.01); *A61B 17/3421* (2013.01); *A61B 2017/00407* (2013.01); *A61B 2017/3429* (2013.01); *A61B 2017/347* (2013.01); *A61B 2017/3488* (2013.01); *A61B 2560/0431* (2013.01)

(58) Field of Classification Search
CPC ............ A61B 17/3421; A61B 17/3423; A61B 2017/347; A61B 2017/3488; A61B 2017/3482; A61B 2017/3492

See application file for complete search history.

(56) References Cited

U.S. PATENT DOCUMENTS

| | | | |
|---|---|---|---|
| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |

(Continued)

FOREIGN PATENT DOCUMENTS

| | | |
|---|---|---|
| DE | 102005047527 A1 | 4/2007 |
| EP | 0480653 A1 | 4/1992 |

(Continued)

OTHER PUBLICATIONS

Extended European Search Report dated Jun. 14, 2021 issued in EP Appln. No. 21155396.1.

*Primary Examiner* — Ashley L Fishback
(74) *Attorney, Agent, or Firm* — Draft Masters IP, LLC

(57) ABSTRACT

A surgical access device including a cannula body and an anchor is disclosed. The cannula body includes a housing, and an elongated portion extending distally from the housing. The elongated portion defines a longitudinal axis and defines a channel extending therethrough. The anchor is disposed in mechanical cooperation with the elongated portion of the cannula body and is longitudinally translatable relative to the elongated portion. The anchor defines an aperture and includes a ratchet mechanism configured to selectively lock a size of the aperture.

19 Claims, 7 Drawing Sheets

(56) References Cited

U.S. PATENT DOCUMENTS

| | | |
|---|---|---|
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,215,531 A | 6/1993 | Maxson et al. |
| 5,222,970 A | 6/1993 | Reeves |
| 5,226,890 A | 7/1993 | Anniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,716,369 A | 2/1998 | Riza |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |

(56) References Cited

U.S. PATENT DOCUMENTS

| | | |
|---|---|---|
| 8,454,645 B2 | 6/2013 | Criscuolo et al. |
| 11,484,337 B2 | 11/2022 | Desjardin et al. |
| 2005/0043685 A1 | 2/2005 | Schinkel-Fleitmann |
| 2009/0182282 A1 | 7/2009 | Okihisa et al. |
| 2010/0057010 A1 | 3/2010 | Goransson |
| 2011/0218620 A1 | 9/2011 | Meiri et al. |
| 2017/0056064 A1 | 3/2017 | Zergiebel et al. |
| 2019/0254703 A1 | 8/2019 | Ciampini et al. |

FOREIGN PATENT DOCUMENTS

| | | |
|---|---|---|
| EP | 0610099 A2 | 8/1994 |
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2015049391 A1 | 4/2015 |
| WO | 2018094478 A1 | 5/2018 |

SURGICAL ACCESS DEVICE INCLUDING ANCHOR WITH RATCHET MECHANISM

CROSS-REFERENCE TO RELATED APPLICATION

The present application is a continuation of U.S. patent application Ser. No. 16/783,505, filed on Feb. 6, 2020, the entire contents of which are incorporated herein by reference.

BACKGROUND

Technical Field

The present disclosure relates to a surgical access device. More particularly, the present disclosure relates to a surgical access device including an anchor with a ratchet mechanism to help maintain its position relative to a patient during a surgical procedure.

Background of Related Art

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e. a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an anchor positioned near a distal end of the surgical access device and adjacent tissue is occasionally used. Positioning and securing such an anchor while the surgical access device is within the body helps minimize undesired movement of the surgical access device with respect to the body.

Accordingly, it may be helpful to provide an anchor with a ratchet mechanism to help maintain the longitudinal position of the surgical access device with respect to the patient.

SUMMARY

The present disclosure relates to a surgical access device including a cannula body and an anchor. The cannula body includes a housing and an elongated portion extending distally from the housing. The elongated portion defines a longitudinal axis and defines a channel extending therethrough. The anchor is disposed in mechanical cooperation with the elongated portion of the cannula body and is longitudinally translatable relative to the elongated portion. The anchor defines an aperture and includes a ratchet mechanism configured to selectively lock a size of the aperture.

In aspects, the ratchet mechanism of the anchor includes a C-shaped clip. The clip may include a first arcuate section and a second arcuate section, where the first arcuate section is movable relative to the second arcuate section.

In aspects, the ratchet mechanism of the anchor includes a clip and a handle, and the handle is pivotable relative to the clip. The ratchet mechanism may include a plurality of teeth disposed on at least one of the first arcuate section of the clip or the second arcuate section of the clip. Movement of the first arcuate section relative to the second arcuate section may change the size of the aperture defined by the anchor. The ratchet mechanism may include a plurality of teeth disposed on the handle of the clip configured to engage the plurality of teeth of the at least one of the first arcuate section of the clip or the second arcuate section of the clip. The handle may include a tab configured to facilitate disengagement of the plurality of teeth of the handle from the plurality of teeth of the at least one of the first arcuate section of the clip or the second arcuate section of the clip.

In additional aspects, the anchor may include a sleeve radially surrounding at least a portion of the clip. The sleeve may be made from foam, gel, or rubber.

The present disclosure also relates to an anchor for use with a surgical access device. The anchor defines an aperture and includes a C-shaped clip, and a handle. The C-shaped clip includes a first arcuate section, a section arcuate section and a backspan interconnecting the first arcuate section and the second arcuate section. The first arcuate section is movable relative to the second arcuate section to change a size of the aperture. At least one of the first arcuate section or the second arcuate section includes a plurality of teeth. The handle is pivotably engaged with the first arcuate section of the C-shaped clip. The handle includes a plurality of teeth configured to engage the plurality of teeth of the at least one of the first arcuate section or the second arcuate section of the C-shaped clip to selectively lock a position of the first arcuate section relative to the second arcuate section.

In aspects, the handle may include a tab configured to facilitate disengagement of the plurality of teeth of the handle from the plurality of teeth of the at least one of the first arcuate section of the clip or the second arcuate section of the clip. The anchor may also include a sleeve radially surrounding at least a portion of the C-shaped clip. The sleeve may be made from foam, gel, or rubber.

DESCRIPTION OF THE DRAWINGS

Various aspects of the present disclosure are illustrated herein with reference to the accompanying drawings, wherein.

DETAILED DESCRIPTION

Figure 1:
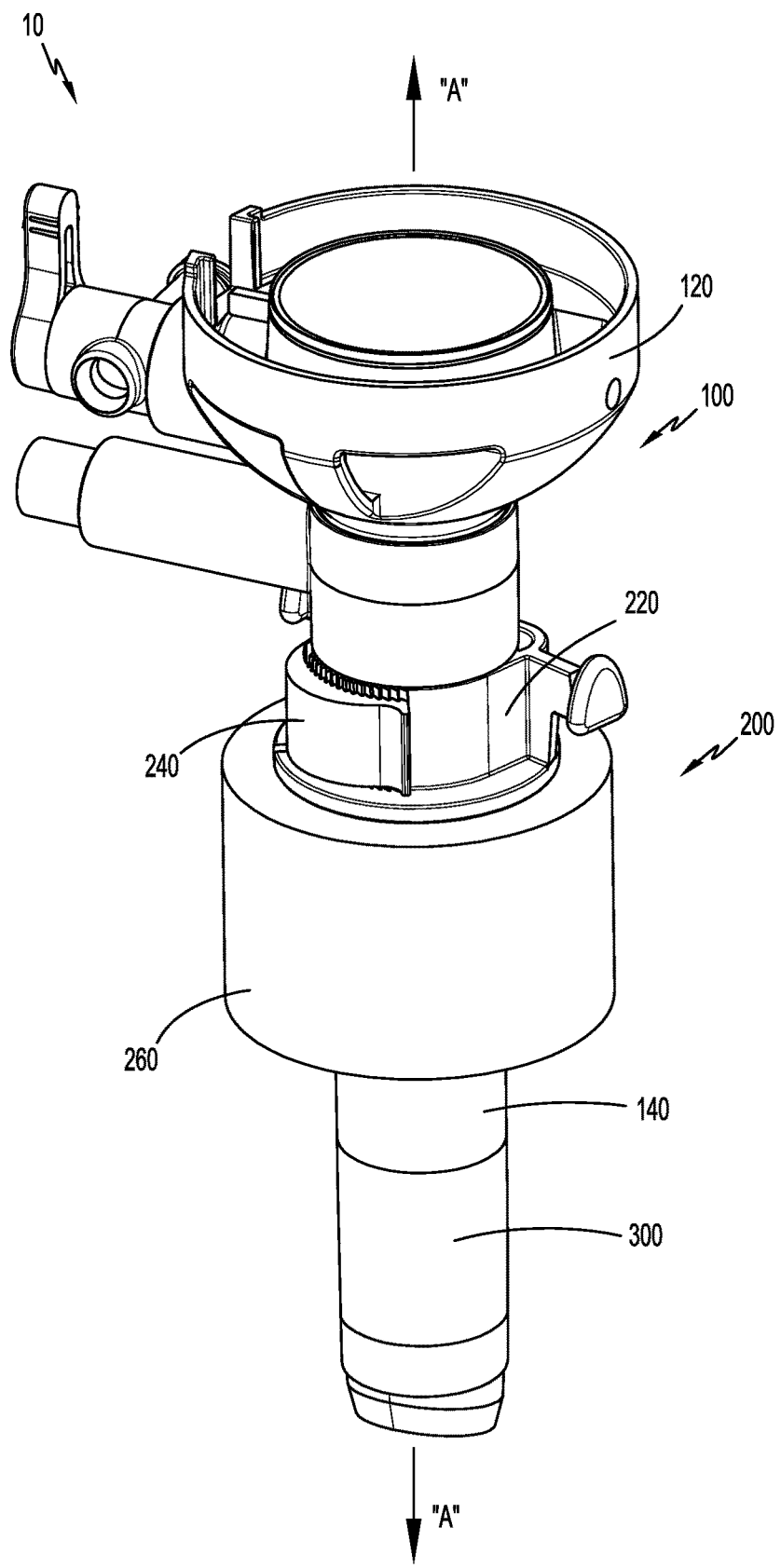
FIG. 1 is a perspective view of a surgical access device including an anchor in accordance with the present disclosure.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

Additionally, the surgical access device of the present disclosure includes an anchor including a ratchet mechanism configured to engage tissue to help maintain the cannula in its position relative to the body during use.

FIGS. 1-10 illustrate a surgical access device according to the present disclosure. With initial reference to FIG. 1, the surgical access device 10 includes a cannula body 100 and an anchor 200. The cannula body 100 includes a proximal housing 120 at its proximal end, and includes an elongated portion 140 extending distally from the proximal housing 120. The elongated portion 140 defines a channel 150 (FIG. 2) extending therethrough, and defines a longitudinal axis "A-A." An obturator (not shown) is insertable through the channel 150 and is engageable with the proximal housing 120, for instance.

Figure 7:
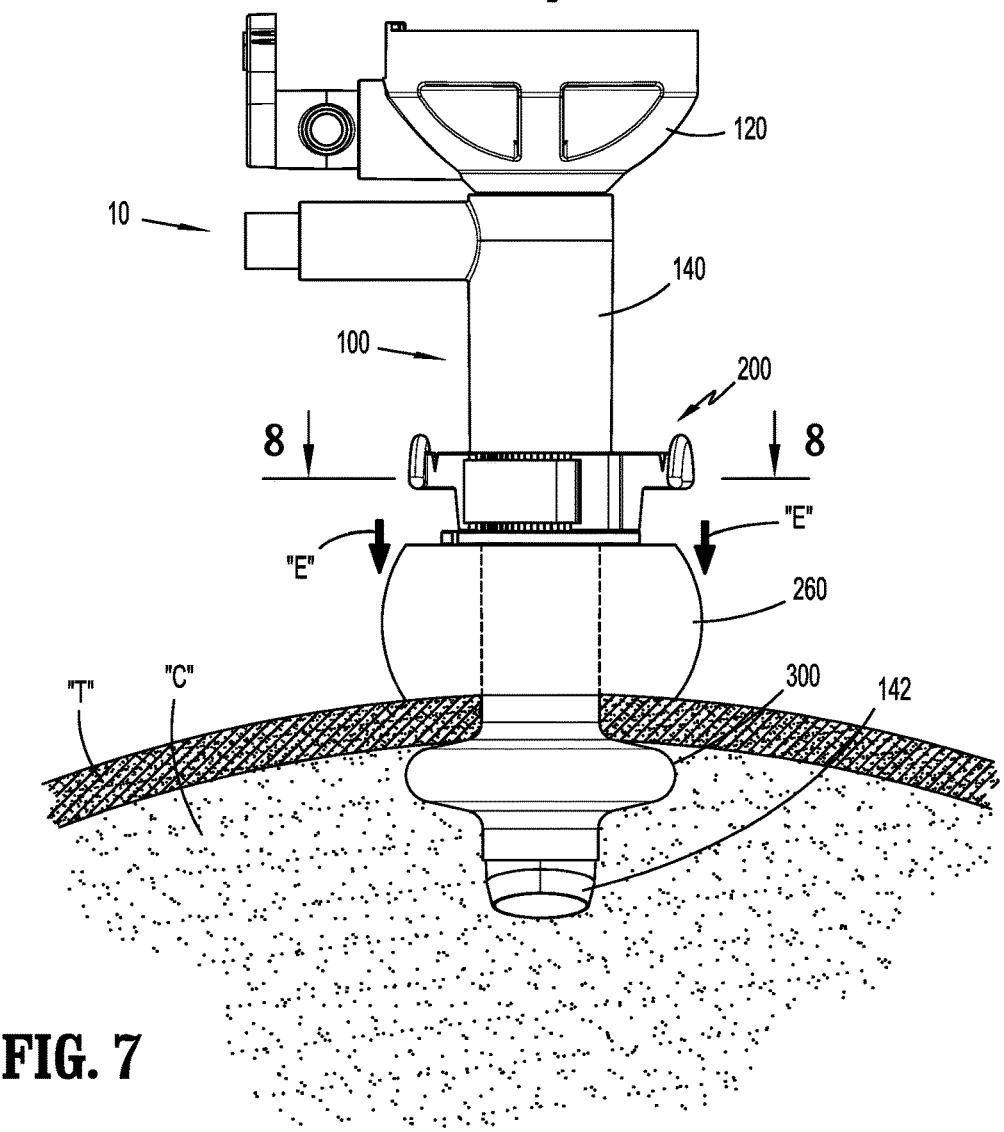
FIG. 7 is a side view of the surgical access device of FIGS. 1 and 2 within tissue illustrating the anchor in a distal position.

The anchor 200 is positionable around the elongated portion 140 of the cannula body 100 such that such that the anchor 200 radially surrounds a portion of the elongated portion 140. More particularly, the anchor 200 is longitudinally translatable along the elongated portion 140 between a first position, where the anchor 200 is farther away from a distal tip 142 of the elongated portion 140 (FIG. 5), and a second position, wherein the anchor 200 is closer to the distal tip 142 of the elongated portion 140 (FIG. 7). Additionally, the anchor 200 is configured to translate longitudinally along the elongated portion 140 of the cannula body 100, and to releasably and selectively lock itself into a desired longitudinal position.

Figure 2:
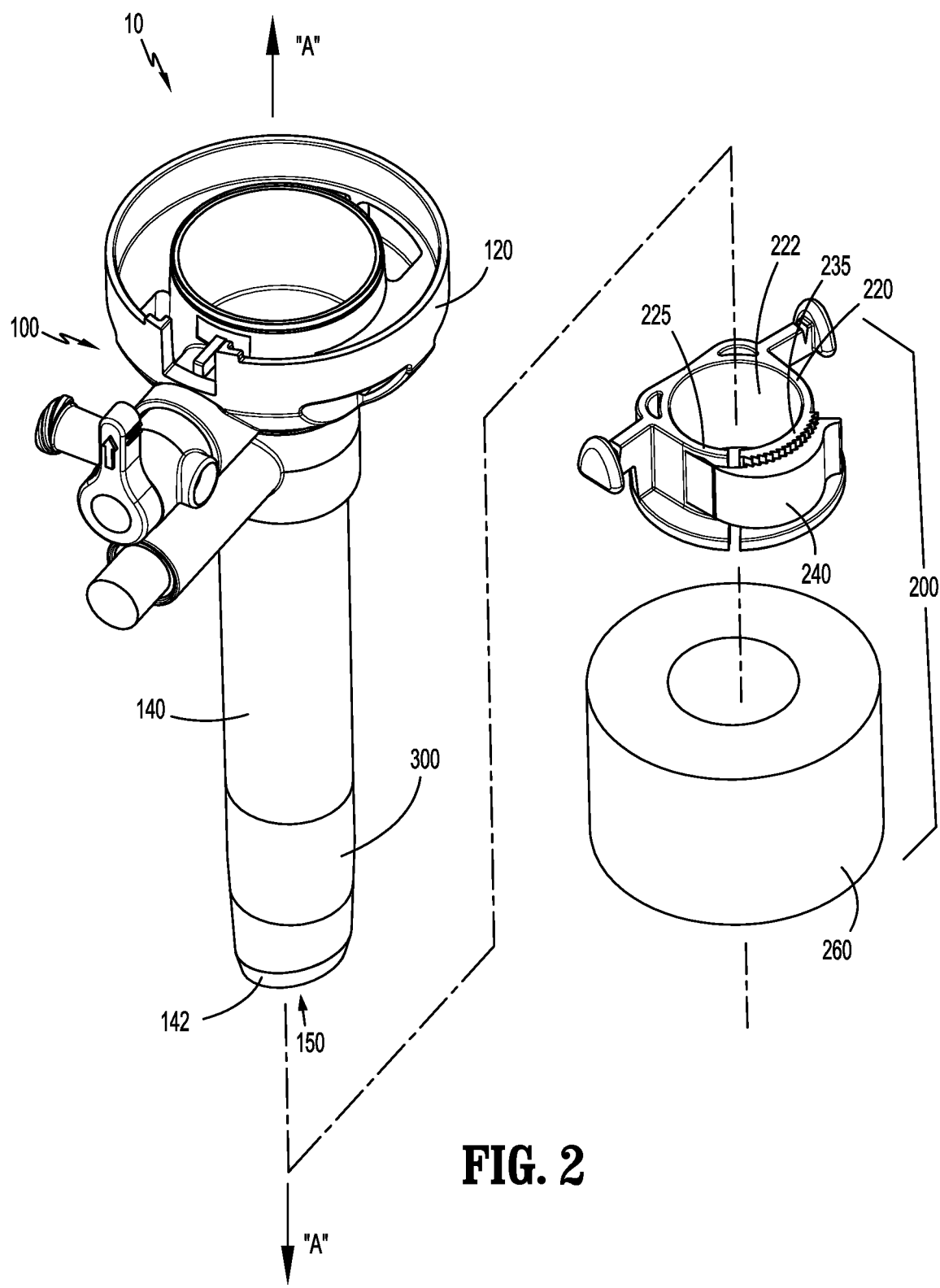
FIG. 2 is an assembly view of the surgical access device of FIG. 1.

Referring to FIGS. 1 and 2, the engagement between the anchor 200 and the cannula body 100 is shown. The anchor 200 includes a clip 220, a handle 240, and a sleeve 260. The clip 220 of the anchor 200 defines an aperture 222, through which the elongated portion 140 of the cannula body 100 is insertable.

Figure 3:
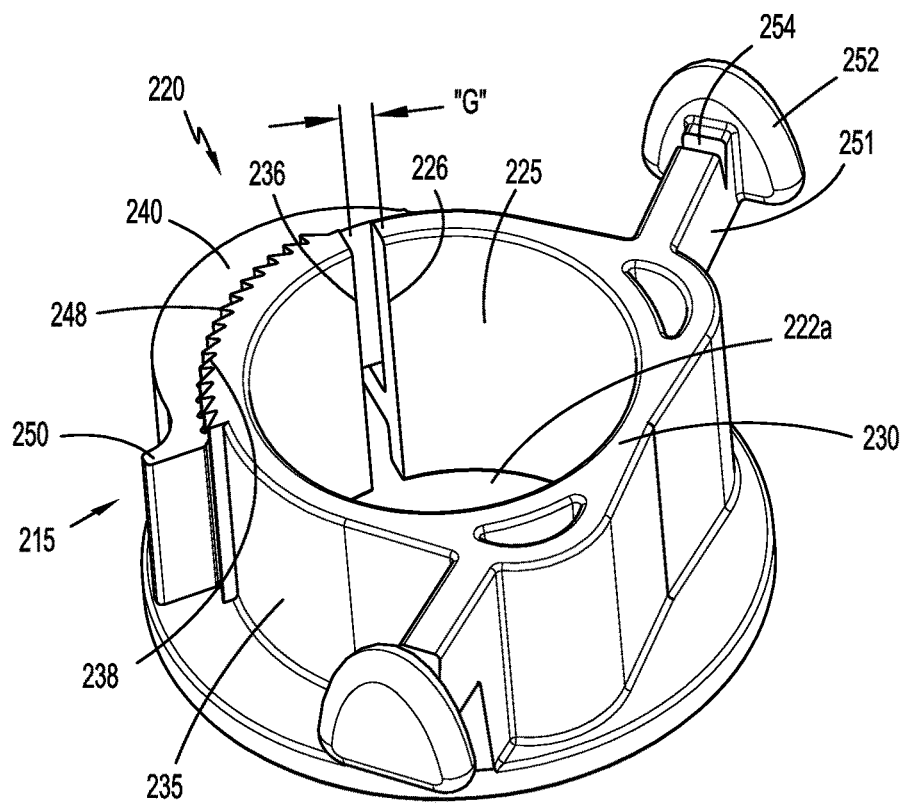
FIGS. 3 and 4 are perspective views of a portion of the anchor of FIGS. 1 and 2.
Figure 4:
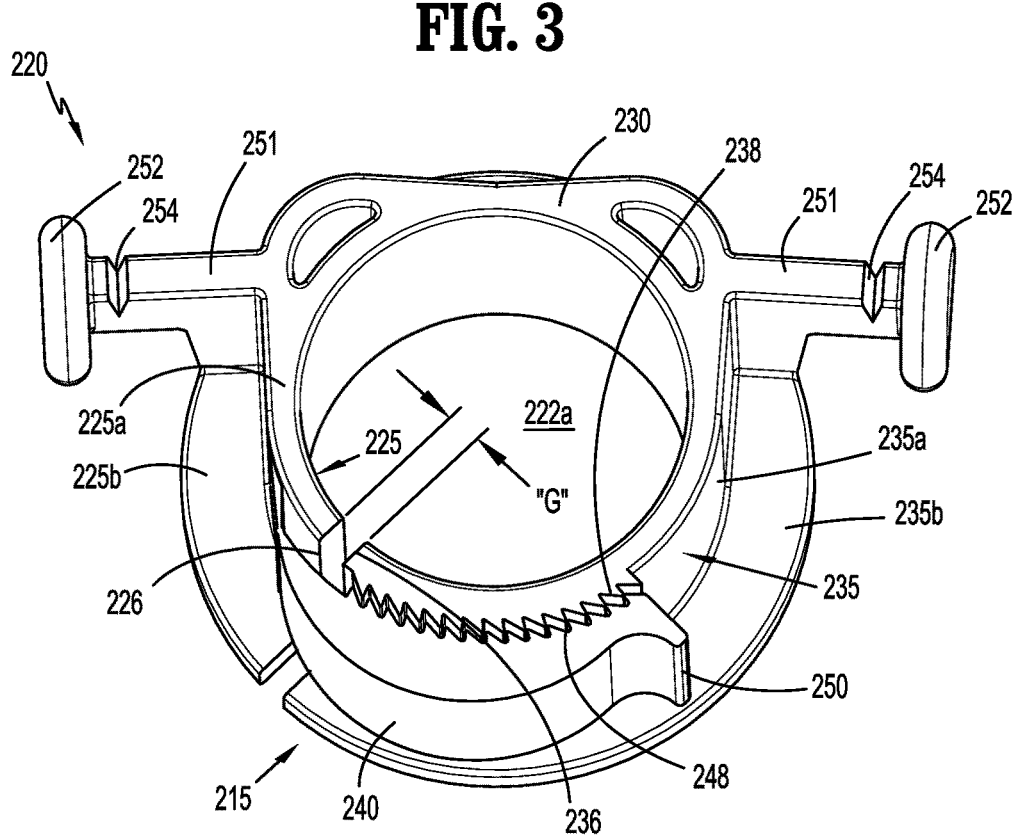
Figure 8:
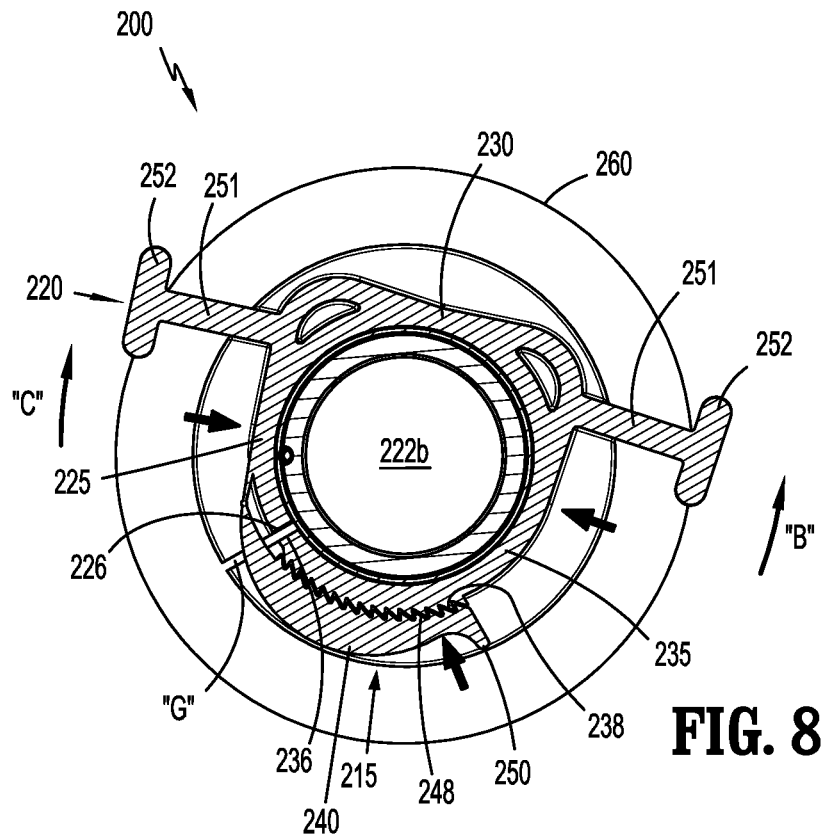
FIG. 8 is a top cross-sectional view of a portion of the surgical access device taken along section line 8-8 in FIG. 7.

FIGS. 3 and 4 illustrate further details of the clip 220 and the handle 240. The clip 220 includes a first arcuate section 225 and a second arcuate section 235, which together define the aperture 222. In aspects, the clip 220 may be C-shaped including an adjustable gap "G" defined between the first arcuate section 225 and the second arcuate section 235. The first arcuate section 225 is movable relative to the second arcuate section 235 (or vice versa) between a first orientation defining a first size aperture 222a (FIGS. 3, 4 and 6) and a second orientation defining a second size aperture 222b (FIG. 8). The first size aperture 222a is larger than the second size aperture 222b; the gap "G" corresponding to the first size aperture 222a is larger than the gap "G" corresponding to the second size aperture 222b. In the first orientation, where the clip 220 defines a larger aperture 222a, the anchor 200 is longitudinally translatable along the elongated portion 140 of the cannula body 100. In the second orientation, where the clip 220 defines a smaller aperture 222b, the anchor 200 is fixed from translating longitudinally along the elongated portion 140 of the cannula body 100. As discussed below, a ratchet mechanism 215 is included on the anchor 200 to selectively lock the size of the aperture 222 defined by the anchor 200.

With continued reference to FIGS. 3 and 4, the handle 240 of the anchor 200 is shown. The handle 240 is arcuate, is coupled to a portion of the clip 220, and is pivotable relative to the clip 220. In the aspects shown in FIGS. 2-4, for instance, the handle 240 is integrally formed with the clip 220 (e.g., molded as a part of the clip 220), and includes a living hinge therebetween.

Figure 9:
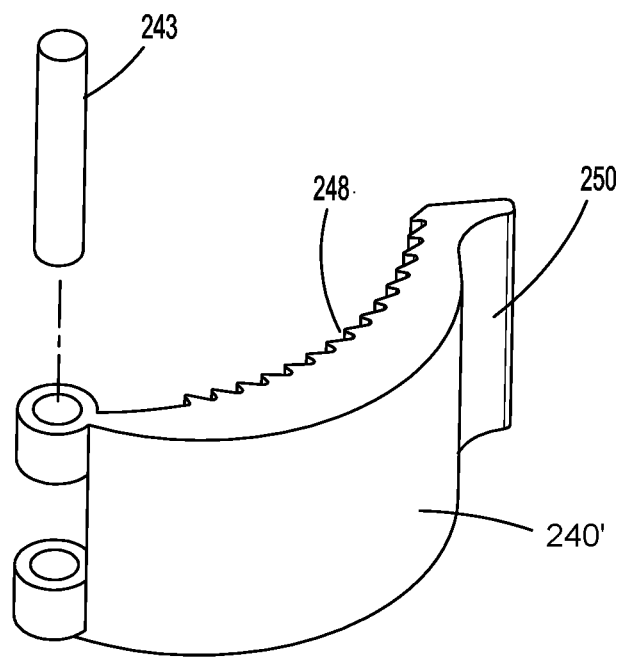
FIG. 9 is an assembly view of a handle of the anchor according to various aspects.
Figure 10:
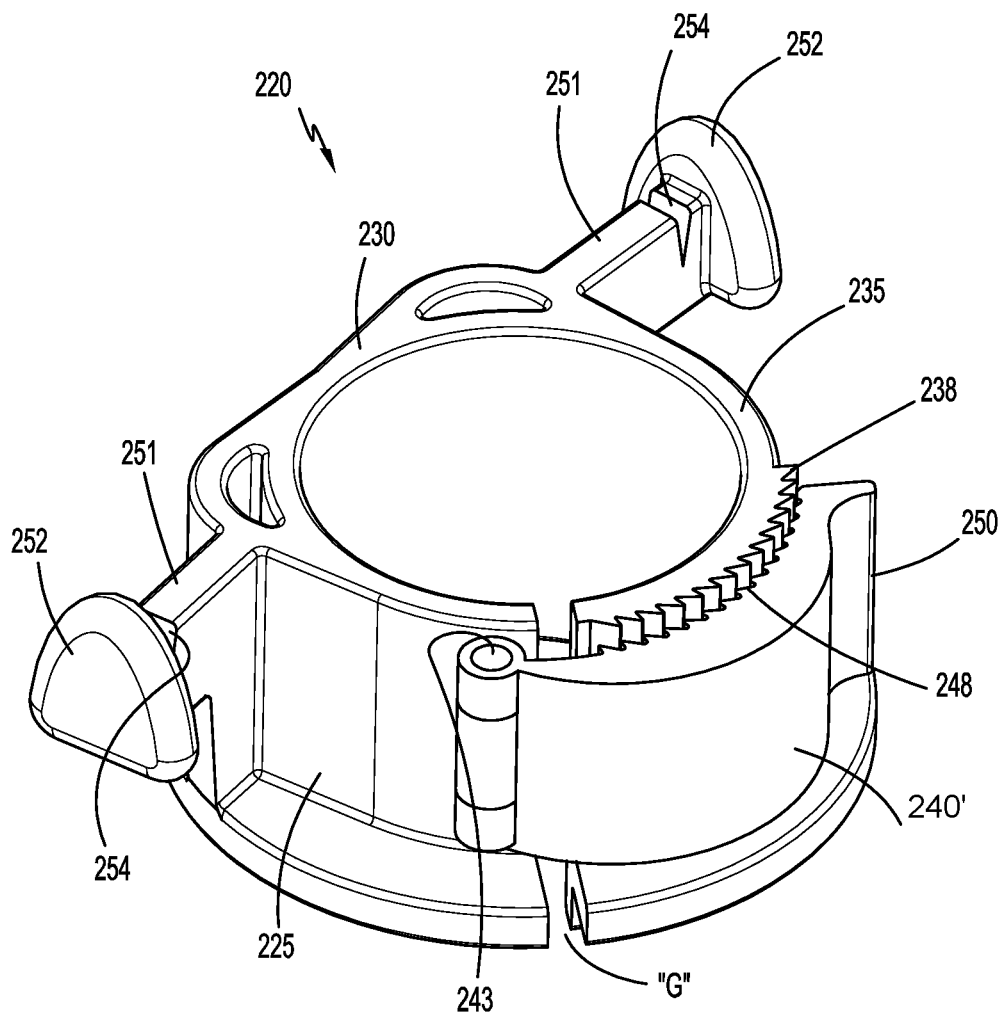
FIG. 10 is a perspective of the anchor including the handle of FIG. 9.

In the aspects shown in FIGS. 9 and 10, for instance, a handle 240' connects to the clip 220 via a pin 243. In the illustrated aspects, the handle 240' is pivotably engaged with the first arcuate section 225 of the clip 220, although the handle may alternatively be engaged with a different portion of the clip 220 (e.g., the second arcuate section 235). As discussed below, pivoting the handle 240' relative to the clip 220 moves the clip 220 between its first orientation and its second orientation.

Referring now to FIGS. 3, 4, 6 and 8, further details of the clip 220 and the handle 240 of the anchor 200 are shown. The first arcuate section 225 and the second arcuate section 235 of the clip 220 each extend from a common backspan 230. The first arcuate section 225 defines a free end 226, which is spaced from the backspan 230, and the second arcuate section 235 defines a free end 236, which is spaced from the backspan 230. Depending on the orientation of the clip 220, a gap "G" is defined between the free end 226 of the first arcuate section 225 and the free end 236 of the second arcuate section 235. As the clip 220 moves from its first orientation to its second orientation, the gap "G" and the aperture 222 defined by the anchor 200 become smaller. In aspects (e.g., depending on the diameter of the elongated portion 140 of the cannula body 100), the free end 226 of the first arcuate section 225 is spaced from the free end 236 of the second arcuate section 235 when the clip 220 is in its second orientation. In other aspects, the free end 226 of the first arcuate section 225 contacts the free end 236 of the second arcuate section 235 when the clip 220 is in its second orientation. In yet other aspects, the free end 226 of the first arcuate section 225 overlaps the free end 236 of the second arcuate section 235 when the clip 220 is in its second orientation.

With continued reference to FIGS. 3, 4, 6 and 8, a ratchet mechanism 215 is shown and is disposed on portions of the clip 220. The ratchet mechanism 215 selectively locks the size of the aperture 222 defined by the anchor 200. The first arcuate section 225 of the clip 220 includes an upper portion 225a and a lower portion 225b, and the second arcuate section 235 of the clip 220 includes an upper portion 235a and a lower portion 235b (FIG. 4). The ratchet mechanism 215 is included on the upper portion 235a of the second arcuate section 235 and on the handle 240. More particularly, the ratchet mechanism 215 includes a plurality of grooves or teeth 238 (i.e., one or more teeth) on the upper portion 235a of the second arcuate section 235, and a plurality of grooves or teeth 248 (i.e., one or more teeth) on the handle 240. The plurality of teeth 238 of the second arcuate section 235 is configured to engage the plurality of teeth 248 of the handle 240 in a ratcheting manner. In particular, the plurality of teeth 238 of the second arcuate section 235 and the plurality of teeth 248 of the handle 240 are angled such that movement of the handle 240 in a first direction (e.g., arrow "B" in FIG. 8) relative to the second arcuate section 235 is facilitated, while movement of the handle 240 in a second, opposite direction (e.g., arrow "C" in FIG. 8) relative to the second arcuate section 235 is hindered or prevented. That is, the plurality of teeth 238 of the second arcuate section 235 and the plurality of teeth 248 of the handle 240 are configured to facilitate incremental movement of the clip 220 from its first orientation toward its second orientation, and effectively locks the clip 220 in a desired position (e.g., when the clip 220 is tight around the elongated portion 140 of the cannula body 100). Additionally, in various aspects, the first arcuate section 225 also includes a plurality of teeth that are configured to engage the plurality of teeth 248 of the handle 240.

As shown in FIGS. 3, 4, 6 and 8-10, the handle 240 also includes a tab 250 extending radially outwardly from an end of the handle 240. The tab 250 is configured to be grasped by a user such that manipulation of the handle 240 is facilitated. More particularly, a user can grasp or press the tab 250 of the handle 240 to move (e.g., pivot) the handle 240 relative to the second arcuate section 235 of the clip 220, such as when moving the clip 220 from its first orientation toward its second orientation. Additionally, a user can move the tab 250 away from the second arcuate section 235 of the clip 220 (in the general direction of arrow "D" in FIG. 6) to effectively unlock the plurality of teeth 248 of the handle 240 from the plurality of teeth 238 of the second arcuate section 235.

In various aspects, the tensile strength of the material of the handle 240 helps the handle 240 remain engaged with the second arcuate section 235. For instance, the handle 240 may be made from plastic or other suitable materials.

As shown in FIGS. 3, 4, 6, 8 and 10, the clip 220 also includes arms 251. The arms 251 are shown extending radially outward from a portion of the clip 220 adjacent the backspan 230. The arms 251 may be useful to grasp while longitudinally translating the anchor 200 along the elongated portion 140 of the cannula body 100. Additionally, each arm 251 includes a finger 252 at an end thereof, and defines a notch 254. The fingers 252 and/or notches 254 can be used as locations to tie sutures to during use, for instance. In aspects, the clip 220 may include more or fewer arms 251 than the two arms 251 that are illustrated. For instance, the clip 220 may not include any arms 251.

The sleeve 260 is shown in FIGS. 1, 2 and 5-8. The sleeve 260 radially surrounds the lower portions 225b, 235b of the first arcuate portion 225 and the second arcuate portion 235, respectively, of the clip 220. In aspects, the sleeve 260 is secured to the clip 220 such that the sleeve 260 and the clip 220 cannot be moved independently of each other. The sleeve 260 is configured to radially expand and contract such that the sleeve 260 remains in contact with the first arcuate portion 225 and the second arcuate portion 235 while the clip 220 transitions between its first and second orientations. Additionally, the sleeve 260 is configured to longitudinally compress in response to being moved against a tissue wall "T," for instance, as indicated by arrows "E" in FIG. 7. The sleeve 260 may be made from foam, gel, rubber (e.g., elastomers), or other suitable compressive material.

Figure 5:
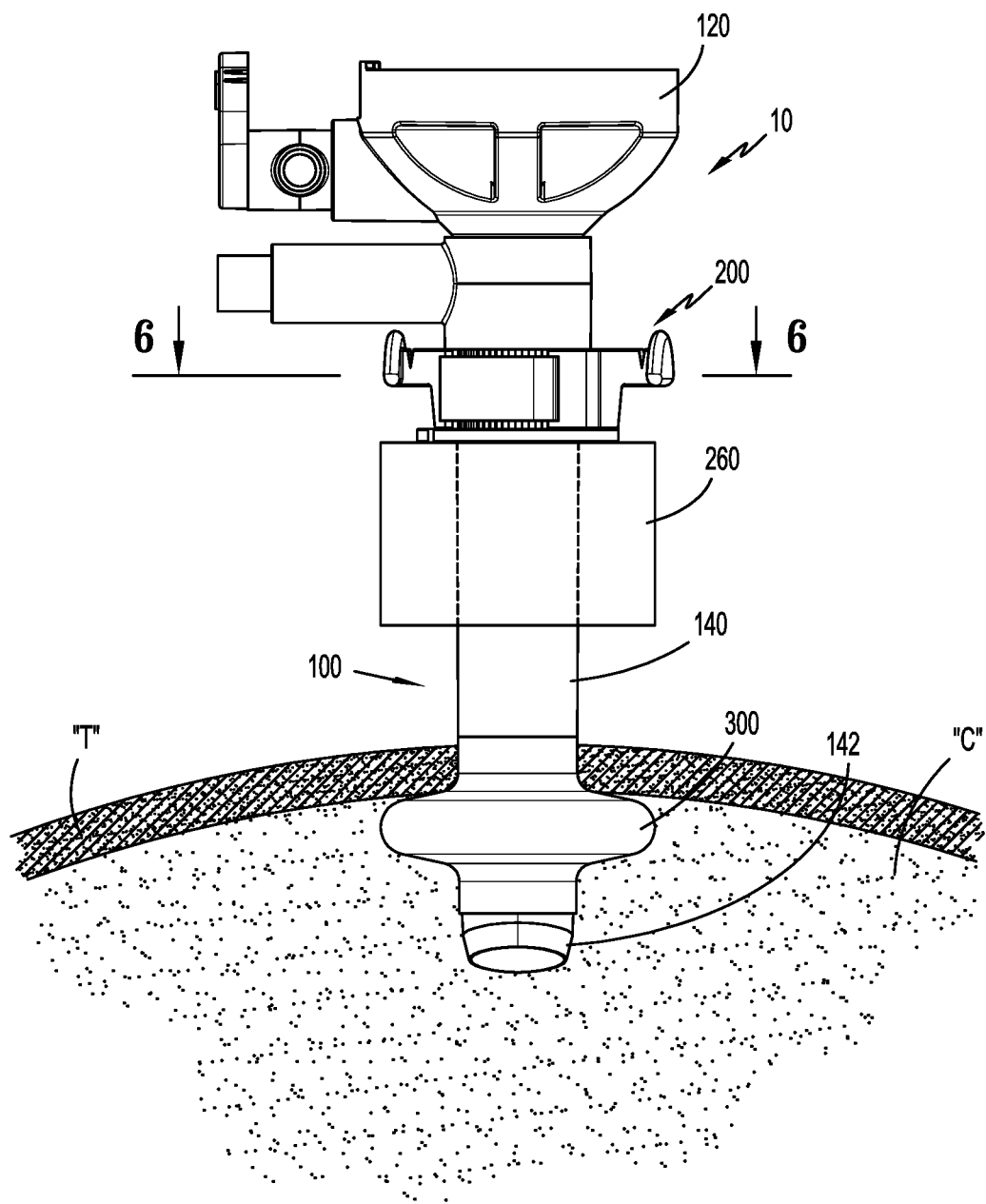
FIG. 5 is a side view of the surgical access device of FIGS. 1 and 2 within tissue illustrating the anchor in a proximal position.
Figure 6:
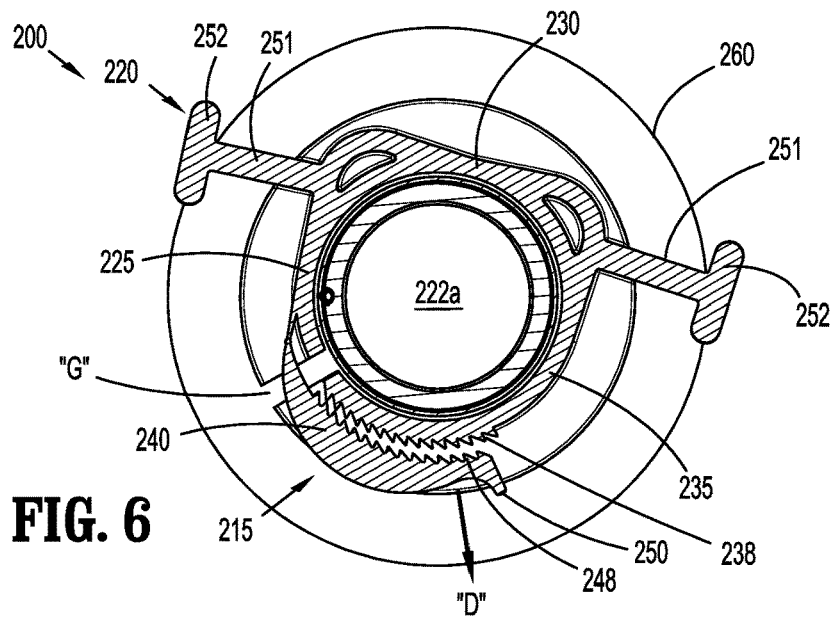
FIG. 6 is a top cross-sectional view of a portion of the surgical access device taken along section line 6-6 in FIG. 5.

Additionally, as shown in FIGS. 1, 2, 5 and 7, the anchor 200 can be used in connection with an additional fixation mechanism 300. For instance, as shown in FIGS. 5 and 7, while the anchor 200 may be positioned along the elongated portion 140 of the cannula body 100 adjacent a proximal wall of tissue adjacent an incision, fixation mechanism 300 can radially extend from the elongated portion 140 of the cannula body 100 and be positioned adjacent a distal wall of the tissue adjacent the incision, for example.

In use, the anchor 200 is initially in a proximal position along the elongated portion 140 of the cannula body 100 as the distal end of the cannula body 100 is being inserted into and/or positioned within the tissue cavity "C" (FIGS. 5 and 7). Next, the fixation mechanism 300, if included, is moved to expanded position (FIGS. 5 and 7), and the cannula body 100 is moved proximally such that the fixation mechanism 300 contacts the distal portion of the tissue wall "T," for instance. Then, the anchor 200 is moved distally along the elongated portion 140 of the cannula body 100 such that the anchor 200 contacts a proximal portion of the tissue wall "T," and the ratchet mechanism 215 is utilized to decrease and lock the size of the aperture 222 such that the anchor is fixed positioned on the elongated portion 140 of the cannula body 100. Here, the tissue wall "T" is sandwiched between the anchor 200 and the fixation mechanism 300 (FIG. 7), and the longitudinal position of the cannula body 100 is fixed relative to the tissue wall "T."

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. An anchor for use with a surgical access device, the anchor comprising:
    a clip defining an aperture;
    a ratchet mechanism disposed on the clip and configured for selectively locking a size of the aperture; and
    a sleeve radially surrounding at least a portion of the clip.

2. The anchor according to claim 1, wherein the ratchet mechanism includes a C-shaped portion.

3. The anchor according to claim 1, wherein the sleeve is spaced apart from the ratchet mechanism.

4. The anchor according to claim 1, wherein the ratchet mechanism includes a handle, the handle being pivotable relative to the clip.

5. The anchor according to claim 1, wherein the clip includes a first arcuate section and a second arcuate section, the first arcuate section being movable relative to the second arcuate section.

6. The anchor according to claim 5, wherein movement of the first arcuate section relative to the second arcuate section changes the size of the aperture defined by the clip.

7. The anchor according to claim 5, wherein the ratchet mechanism includes a plurality of teeth disposed on at least one of the first arcuate section of the clip or the second arcuate section of the clip.

8. The anchor according to claim 1, wherein the sleeve forms a complete ring.

9. The anchor according to claim 1, wherein the sleeve is made from foam, gel, or rubber.

10. An anchor for use with a surgical access device, the anchor comprising:
   a clip defining an aperture and including a first arcuate section and a section arcuate section, the first arcuate section movable relative to the second arcuate section to change a size of the aperture, at least one of the first arcuate section or the second arcuate section includes a plurality of teeth; and
   a handle pivotably engaged with the first arcuate section of the clip, the handle including a plurality of teeth configured to engage the plurality of teeth of the at least one of the first arcuate section or the second arcuate section to selectively lock a position of the first arcuate section relative to the second arcuate section.

11. The anchor according to claim 10, wherein the handle includes a tab for facilitating disengagement of the plurality of teeth of the handle from the plurality of teeth of the at least one of the first arcuate section of the clip or the second arcuate section of the clip.

12. The anchor according to claim 10, further including a sleeve radially surrounding at least a portion of the clip.

13. The anchor according to claim 12, wherein the sleeve is made from foam, gel, or rubber.

14. The anchor according to claim 12, wherein the sleeve forms a complete ring.

15. The anchor according to claim 10, further including a sleeve extending distally from the clip and radially surrounding a distal portion of the clip.

16. An anchor for use with surgical access device, the anchor comprising:
   a clip defining an aperture and including a first arcuate section and a second arcuate section, the first arcuate section movable relative to the second arcuate section;
   a ratchet mechanism disposed in mechanical cooperation with the clip for selectively locking a size of the aperture; and
   a sleeve radially surrounding at least a portion of the clip.

17. The anchor according to claim 16, wherein the sleeve forms a complete ring.

18. The anchor according to claim 16, wherein the sleeve is spaced apart from the ratchet mechanism.

19. The anchor according to claim 16, wherein the sleeve is made from at least one of foam, gel, or rubber.

* * * * *